United States Patent
Ho et al.

(10) Patent No.: US 8,476,229 B2
(45) Date of Patent: Jul. 2, 2013

(54) BLOOD SUGAR-MODULATING POLYPEPTIDES

(75) Inventors: Tin-Yun Ho, Taichung (TW); Chien-Yun Hsiang, Taichung (TW)

(73) Assignee: China Medical University, Taichung (TW)

( * ) Notice: Subject to any disclaimer, the term of this patent is extended or adjusted under 35 U.S.C. 154(b) by 322 days.

(21) Appl. No.: 12/949,196

(22) Filed: Nov. 18, 2010

(65) Prior Publication Data

US 2011/0124557 A1 May 26, 2011

Related U.S. Application Data

(62) Division of application No. 12/392,672, filed on Feb. 25, 2009, now abandoned.

(30) Foreign Application Priority Data

Dec. 1, 2008 (TW) .............................. 97146586 A (51) Int. Cl.
*A61K 38/04* (2006.01)
*A61P 3/08* (2006.01)
*A61P 3/10* (2006.01)

(52) U.S. Cl.
USPC .......................................... 514/6.8; 514/6.9

(58) Field of Classification Search
None
See application file for complete search history.

(56) References Cited

U.S. PATENT DOCUMENTS 6,800,726 B1 * 10/2004 Rao et al. ...................... 530/300

FOREIGN PATENT DOCUMENTS

| CN | 101081244 | 12/2007 |
|---|---|---|
| JP | 2001278804 | 10/2001 |
| JP | 2002516608 | 6/2002 |
| JP | 2003169621 | 6/2003 |
| WO | 2005009351 | 2/2005 |

OTHER PUBLICATIONS

Office Action, dated Dec. 31, 2010, received in counterpart Taiwan Patent Application No. 79146586, 12 pgs. (including cover page with abstract from related EP 2 191 837 A1).
Database UniProt [Online], Dec. 15, 2003, SubName: Full=Trypsin inhibitor MCI-3, integrated into UniProtKB/Swiss-Prot, ID No. Q7M1Q1, (Office Action Citation No. D2), 4 pgs.
Database UniProt [Online], Jul. 1, 1989, SubName: Full=Trypsin inhibitor BGIT, integrated into UniProtKB/TrEMBL, ID No. ITI3, (Office Action Citation No. D3), 5 pgs.
Database UniProt [Online], Mar. 1, 1992, SubName: Full=Glu S.griseus protease inhibitor, integrated into UniProtKB/Swiss-Prot, ID No. BGIA, (Office Action Citation No. D4), 6 pgs.
Database UniProt [Online], Jun. 12, 2007, SubName: Full=Putative uncharacterized protein, integrated into UniProtKB/TrEMBL, ID No. A5C3XA, (Office Action Citation No. D6), 5 pgs.
Database UniProt [Online], Jul. 5, 2004, SubName: Full=Protease inhibitor, integrated into UniProtKB/TrEMBL, ID No. Q6YEY6, (Office Action Citation No. D7), 6 pgs.
Database UniProt [Online], Mar. 20, 2007, SubName: Full=Putative uncharacterized protein, integrated into UniProtKB/TrEMBL, ID No. A2YVM2, (Office Action Citation No. D8), 5 pgs.
Document cited as D11 in the Office Action, dated Dec. 31, 2010, received in counterpart Taiwan Patent Application No. 79146586, with English abstract entitled, "To examine the active components of bitter gourd extracts for regulating the blood sugar," 22 pgs.
European Search Report dated Mar. 23, 2010, pp. 6.
Database UniProt [Online], Nov. 1, 1996, "SubName: Full=Pathogenesis-related protein PR-6 type; Flags: Fragment;" XP002572258 retrieved from EBI accession No. UNIPROT: Q41361 Database accession No. Q41361 * compound *.
Office Action, dated Nov. 24, 2010, received in Japanese Patent Application No. 2009062569, 5 pgs.
Miura, et al., "Isolation and Amino Acid Sequences of Two Trypsin Inhibitors from the Seeds of Bitter Gourd (*Momordica charantia*)," Biosci. Biotech. Biochem., 1995, pp. 469-473, 59(3).
Uebanso, et al., "Extracts of *Momordica charantia* Suppress Postprandial Hyperglycemia in Rats," J. Nutr. Sci. Vitaminol., 2007, pp. 482-288, 53.
Donya, et al., "Effects of Processing Methods on the Proximate Composition and Momordicosides K and L Content of Bitter Melon Vegtable," Journal of Agricultural and Food Chemistry, 2007, pp. 5827-5833, 55.
Yibchok-Anun, "Slow Acting Protein Extract from Fruit Pulp of *Momordica charantia* With Insulin Secretagogue and Insulinomimetic Activities," Biol. Pharm. Bull. 2006, pp. 1126-1131, 29(6).

* cited by examiner

*Primary Examiner* — Daniel C Gamett
(74) *Attorney, Agent, or Firm* — McClure, Qualey & Rodack, LLP (57) ABSTRACT

A blood sugar-modulating polypeptide, a pharmaceutical composition comprising the polypeptide, and a method for modulating blood sugar in a mammal comprising the administration of the polypeptide are provided. The polypeptide has a following amino acid sequence or a homologous amino acid sequence derived from the substitution, deletion, and/or addition of one or more amino acids therein:

RVRVWVTERGIVARPPTIG (SEQ ID NO. 11).

11 Claims, 2 Drawing Sheets

BLOOD SUGAR-MODULATING POLYPEPTIDES

CROSS-REFERENCE TO RELATED APPLICATION

This application is a divisional of U.S. patent application Ser. No. 12/392,672, filed on 25 Feb. 2009, entitled "Blood Sugar-Modulating Polypeptides," the entire disclosure of which is incorporated herein by reference. This application also claims priority to Taiwan Patent Application No. 097146586 filed on Dec. 1, 2008, the disclosure of which is incorporated herein by reference in its entirety.

BACKGROUND OF THE INVENTION

1. Field of the Invention

The present invention provides a blood sugar-modulating polypeptide and its use, especially to a polypeptide with the following amino acid sequence or a homologous amino acid sequence derived from the substitution, deletion, and/or addition of one or more amino acids therein:

```
RVRVWVTERGIVARPPTIG      (SEQ ID NO. 11).
```

2. Descriptions of the Related Art

Diabetes is a chronic illness of metabolic abnormality. The main cause of diabetes is a lack of insulin, a defective function of insulin in the body, or the resistance to insulin caused by the combination of innate gene defects and the postnatal environment, leading to the low ability of using sugar, or even leading to the complete loss of the ability, thus further elevating blood sugar and abnormalizing the metabolism of proteins and lipids in the body. In addition, diabetes brings other chronic complications, including the pathological changes of the ocular fundus, nerve (including motor nerve, sensory nerve, and autonomic nerve), kidney, great vessels (including cerebrovascular obstruction, coronary artery disease, the occlusion of peripheral vessels), diabetes foot, etc.

According to the statistics from the World Health Organization (WHO), the number of diabetes patients around the world has increased dramatically, from about 30 million in 1985 to about 135 million in 1995, and to more than 177 million at present. The WHO further indicates that the number of worldwide diabetes patients will be more than 336 million in 2030. Moreover, the medical cost for diabetes and its complications in the U.S. increased from 44 billion USD in 1997 to 132 billion USD in 2000. With the increased prevalence of diabetes, it is important to develop a substance or medication that can modulate blood sugar efficiently.

Since 1922, insulin has been mainly used for treating diabetes. However, the lack of insulin is only part of the cause for the abnormality of pancreas function. Hence, using insulin individually to treat diabetes has limited efficiency.

Besides insulin, there are other pharmaceutical agents used to treat diabetes. These pharmaceutical agents, used for reducing blood sugar, can be classified into five groups according to their mechanisms. The first group consists of sulfonylureas, which promote the secretion of insulin from the pancreas and increase the number of insulin receptors of histiocytes. The second group consists of benzoic acid derivatives, capable of stimulating the secretion of insulin. The third group consists of biguanides, which inhibit the absorption of sugar in the stomach or intestine, inhibit the production of sugar in the liver, and promote the intake of sugar in tissues. The fourth group consists of α-glucosidase inhibitors, which prevent disaccharides from being degraded into monosaccharides so they can be absorbed by the intestines. The fifth group consists of insulin sensitizers, which alleviate the resistance of peripheral tissues and hepatocytes to insulin. Nevertheless, each group of the aforesaid pharmaceutical agents has different side effects. For example, sulfonylureas may cause rashes and a low level of blood sugar; benzoic acid derivatives may decrease the level of blood sugar; biguanides may cause lactic acidosis and stomach and intestine illnesses; α-glucosidase inhibitors may cause stomach and intestine illnesses; and insulin sensitizers may lead to the abnormality of liver function and injury to hepatocytes. Accordingly, it is important to develop medication with a blood sugar-modulating function and without side effects.

Unlike common compounds, polypeptides have better metabolizability and receptibility for organisms, and thus have fewer side effects. Therefore, many polypeptides have been studied in the world for decades and have been applied in clinical treatment. For instance, TW 1283684 discloses a Glucagon-Like Peptide-1 analogue, which reduces blood sugar, while U.S. Pat. No. 7,393,919 discloses medication for reducing blood sugar using Human prolslet Peptide (HIP), wherein the HIP is an active fragment of a pancreatitis-associated protein precursor.

Furthermore, polypeptides have been found to have blood sugar-reducing activity and can be obtained from plant extracts. For example, U.S. Pat. No. 6,127,338 discloses a polypeptide with blood sugar-reducing activity from bitter melon. The amino acid sequence of the polypeptide is KTNMKHMAGAAAAGAVVG (SEQ ID NO. 13), and the molecular weight of the polypeptide is less than 10 kDa.

Consequently, even though there are a lot of pharmaceutical agents for modulating blood sugar, a single or combined treating method or a pharmaceutical composition for treating diabetes with different morbific mechanisms is still needed.

The present invention researches the aforesaid requirement, and provides a novel polypeptide with a blood sugar-modulating function, especially a blood sugar-modulating function for animals in the normal state or in the diabetic state.

SUMMARY OF THE INVENTION

One objective of this invention is to provide a polypeptide for modulating blood sugar, comprising the following amino acid sequence or a homologous amino acid sequence derived from the substitution, deletion, and/or addition of one or more amino acids therein:

```
RVRVWVTERGIVARPPTIG      (SEQ ID NO. 11).
```

Preferably, the polypeptide of the present invention comprises one or more amino acid sequences selected from a group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and a homologous amino acid sequence derived from the substitution, deletion, and/or addition of one or more amino acids therein.

Another objective of this invention is to provide a pharmaceutical composition for modulating blood sugar, comprising the polypeptide of the present invention.

Yet a further objective of this invention is to provide a method for modulating blood sugar in a mammal, comprising the administration of the polypeptide of the present invention.

The present invention also provides an isolated polynucleotide, encoding the polypeptide of the present invention.

The detailed technology and preferred embodiments implemented for the subject invention are described in the following paragraphs for people skilled in this field to well appreciate the features of the claimed invention.

DESCRIPTION OF THE PREFERRED EMBODIMENT

Unless there is an explanation in this article otherwise, the words "a", "an", "the", and other analogous words in this specification (especially in the following claims) should be considered as a singular or plural form.

The term "homologous polypeptide" in this specification represents a polypeptide with an amino acid sequence derived from the substitution, deletion, and/or addition of one or more amino acids in the amino acid sequence of a particular polypeptide; that is, a homologue of the particular polypeptide.

The polypeptide for modulating blood sugar of the present invention comprises a following amino acid sequence or a homologous amino acid sequence derived from the substitution, deletion, and/or addition of one or more amino acids therein:

```
RVRVWVTERGIVARPPTIG      (SEQ ID NO. 11).
```

[A]ccording to the present invention, the homologous amino acid sequence has a sequence identity of at least about 28% to the amino acid sequence: RVRVWVTERGIVARPPTIG (SEQ ID NO. 11). For example, the homologous amino acid sequence may have a sequence identity of at least about 50%, about 53%, about 58%, about 63%, about 68% or about 74% to said amino acid sequence.

Preferably, the polypeptide of the present invention comprises one or more amino acid sequences selected from a group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and a homologous amino acid sequence derived from the substitution, deletion, and/or addition of one or more amino acids therein.

More preferably, the polypeptide of the present invention comprises one or more amino acid sequences selected from a group consisting of SEQ ID NO: 4, SEQ ID NO: 7, SEQ ID NO: 9, SEQ ID NO: 10, SEQ ID NO: 11, SEQ ID NO: 12, and a homologous amino acid sequence derived from the substitution, deletion, and/or addition of one or more amino acids therein.

The polypeptide of the present invention can be obtained by plant extraction, artificial synthesis, gene recombination technique, or a combination thereof. The artificial synthesis herein means that, depending on the desired polypeptide, amino acids can be linked in sequence by a manual method, including chemical synthesis methods or a method using a peptide synthesizer applying the principle of chemical synthesis. Accordingly, the artificial synthesis method generally has the following advantages: changing the primary structure of a polypeptide easily during the synthesis process, adding a particular amino acid conveniently, and modifying the terminal of a polypeptide expediently.

The chemical synthesis methods that can be used to synthesize the polypeptide of the present invention can be divided into a solid phase synthesis method and a liquid phase synthesis method. Generally, the liquid phase synthesis method has to carry out an extraction operation after every linkage step of each amino acid. In addition, a chromatographic purification step is also needed since the peptide intermediates from the extraction are usually mixtures. In other words, using the liquid phase synthesis method to synthesize polypeptides involves the complicated extraction and chromatographic purification steps to obtain products with high purity.

Unlike the liquid phase synthesis method, the solid phase synthesis method is performed in quite a different way. The linkage reaction of amino acids occurs on the solid polymer particle (or a polymer support) in a solvent. In this method, the N-terminal amino acid of a desired polypeptide is first covalently linked to a polymer particle, and then other amino acids are linked in sequence with a specific linkage method. Eventually, the polypeptide is completed. Because the polymer particle does not dissolve in the solvent, the polymer particle (and the desired polypeptide connected to the polymer particle) can be separated from the reaction reagents and side products by a washing and filtering operation after the synthesis process. That is, only one purification step is required in the end of the whole synthesis process in the solid phase synthesis method. Hence, unlike the liquid phase synthesis method, the solid phase synthesis method is relatively convenient and can reduce synthesis time significantly, and thus it is more advantageous in terms of the synthesis of long-chain polypeptides.

Presently, many kinds of apparatuses for synthesizing polypeptides automatically have been developed, for instance, solid phase peptide synthesizers, liquid phase peptide synthesizers, microwave peptide synthesizers, etc. They all can be opted for synthesizing the polypeptide of the present invention depending on the requirements.

The polypeptide of the present invention also can be synthesized by the gene recombination technique. Herein, an expression vector containing a polynucleotide encoding the polypeptide of the present invention is placed in a host cell, and the polynucleotide is then expressed to produce the polypeptide of the present invention. The host cell can be *Escherichia coli* or yeast, and the expression vector can be selected from common vectors available from the market, for example, pQStrep2, pQStrep4, pGEX-6P1, pQTEV, etc.

Figure 1:
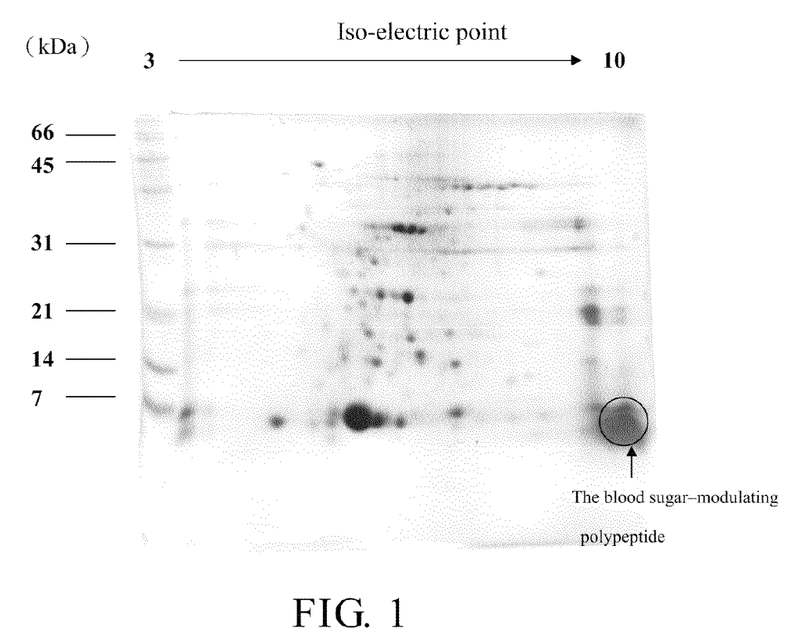
FIG. 1 is a figure of the two-dimensional gel electrophoresis of the polypeptide of the present invention.

Moreover, the polypeptide of the present invention also can be obtained from plant extracts. There are several polypeptides capable of modulating blood sugar that can be obtained from the extracts of plants from the cucumber family, such as bitter melon, kakorot, cucumber, pumpkin, gourd, watermelon, snake gourd seed, snake gourd root, and combinations thereof. It has been proved by protein electrophoresis that the polypeptides able to modulate blood sugar in the extracts of the plants from the cucumber family all belong to the homologous polypeptide (as shown in FIG. 1). Nonetheless, the polypeptide of the present invention also can be obtained from plants beside the plants from the cucumber family, such as *Zinnia elegans, Medicago truncatula*, grape, grapefruit, *Sambucus nigra, Arabidopsis thaliana*, rice, and combinations thereof. That is, the source of the polypeptide of the present invention is not limited to the plants from the cucumber family.

For example, the plant extract from bitter melon can be acquired by the following steps. Thereafter, the polypeptide of the present invention can be obtained by purifying the plant extract (for instance, using protein electrophoresis or chromatographic purification). First, a bitter melon is macerated in a solvent to obtain a crude suspension, wherein the solvent can be phosphate buffer, citrate buffer, water, and so on. The bitter melon can be disintegrated by a blender or a grinder. Particles in the crude suspension are removed from the liquid phase by a centrifuge at a speed of 12,000 rpm to 15,000 rpm, and then a resultant supernatant is filtered using a filter with a pore size of 0.1 µm to 0.5 µm. A resultant filtrate is then passed through a membrane filter with a 1 kDa cut-off, and a resultant supernatant is then passed through a membrane filter with a 10 kDa cut-off. Eventually, a resultant filtrate is collected to obtain a water-soluble bitter melon extract containing the polypeptide of the present invention. The membrane filter can be selected from conventional membrane filter products, such as Amicon® membrane filter, Millipore® membrane filter, etc. Then, the desired polypeptide can be isolated by using a purification method, such as protein electrophoresis or chromatographic purification. Finally, a preservative (e.g. sodium benzoate, salicylic acid, etc.) can be added optionally. And, the polypeptide is stored at −80° C.

In using protein electrophoresis to isolate the polypeptide of the present invention, two-dimensional gel electrophoresis can be used specifically to isolate the polypeptide. First, the above resultant water-soluble bitter melon extract is subjected to protein precipitation, and then the protein precipitate is then subjected to one-dimensional iso-electric focusing (IEF). On the second day, a SDS-PAGE (sodium dodecyl sulfate-polyacrylamide gel electrophoresis) gel is prepared, injected into a gel slot, and flattened by using ethanol. After twenty minutes, the ethanol is poured out from the gel slot, and the gel strip treated by the IEF and a protein molecular weight marker is injected into a sample well, respectively. Electrophoresis is then carried out by using electric current at 110 volts. Electrophoresis ends when the dye moves to the bottom of the gel. The gel is then removed from the gel slot and is stained with a stain reagent. Then, the stain reagent on the gel is removed by using a wash buffer, and the gel is decolorized by using a destain buffer. Finally, a protein band at the position of the iso-electric point of 9 to 10, and of the molecular weight of 1 kDa to 7 kDa on the gel is cut and collected, and then the polypeptide of the present invention is obtained.

Moreover, the polypeptide of the present invention can also be obtained by a combination of the aforesaid methods. For example, a fragment of the desired polypeptide can be first acquired by gene recombination or plant extraction, and then the complete polypeptide can be obtained by artificial synthesis.

The polypeptide of the present invention can be used to produce a medication for reducing blood sugar. Hence, the present invention also provides a pharmaceutical composition for modulating blood sugar, comprising an effective amount of the polypeptide of the present invention and a pharmaceutically acceptable carrier. The pharmaceutical composition may be of any suitable dosage forms, such as a tablet, a capsule, a granule, a powder, a fluid extract, a solution, a syrup, a suspension, an emulsion, a tincture, an injection, an intravenous injection, a powder injection, a suspension injection, a powder-suspension injection, or a combination thereof, etc.

In addition, the pharmaceutical composition of the present invention may optionally contain other adjuvants, such as a solvent, a dispersion medium, a coating, a stabilizer, a thinner, a preservative, a conservative, an antiseptic, an anti-fungus reagent, an isotonic reagent, an absorption-retarding reagent, a disintegrant, an emulsifier, a binder, a lubricant, a pigment, etc. There is no particular limit on the adjuvant as long as it does not influence the activity of the polypeptide adversely. For example, the solvent can be water or a sucrose solution; the thinner can be lactose or starch; the preservative can be benzyl alcohol; the absorption-retarding reagent can be chitosan or glycosaminoglycan; the lubricant can be magnesium carbonate; and the pigment can be tartrazine.

To prevent the polypeptide from being degrading by enzymes in the alimentary canal, the pharmaceutical composition of the present invention can be administrated by injection, and is brought to a released position directly by the blood. When the pharmaceutical composition of the present invention is administrated by oral administration, the pharmaceutical composition may contain an absorbance-retarded reagent to protect itself from the stomach acids and enzymes in the front half segment of the small intestine.

When the pharmaceutical composition containing the polypeptide of the present invention is used to modulate the blood sugar of humans or animals, the dosage is 50 mg/kg-body weight daily with oral administration, based on the amount of the polypeptide. If the injection administration is applied, the daily effective dosage of the pharmaceutical composition for modulating blood sugar is $2.5 \times 10^{-9}$ mole/kg-body weight.

The present invention further provides an isolated polynucleotide, encoding the polypeptide of the present invention. The polynucleotide can be obtained by a conventional clone method. For instance, a genomic deoxyribonucleic acid can be first extracted from a plant cell, and then is used as a template for a polymerase chain reaction. After the polymerase chain reaction is completed, a product is purified to provide the isolated polynucleotide of the present invention.

The present invention yet provides a method for modulating blood sugar in a mammal, especially in a human, comprising the administration of the polypeptide of the present invention. The polypeptide can be administrated as any suitable form, such as a pharmaceutical composition. The dosage form of the pharmaceutical composition is as described above. With the blood sugar-modulating activity of the polypeptide of the present invention, the method of the present invention is especially useful for treating diabetes.

Figure 2:
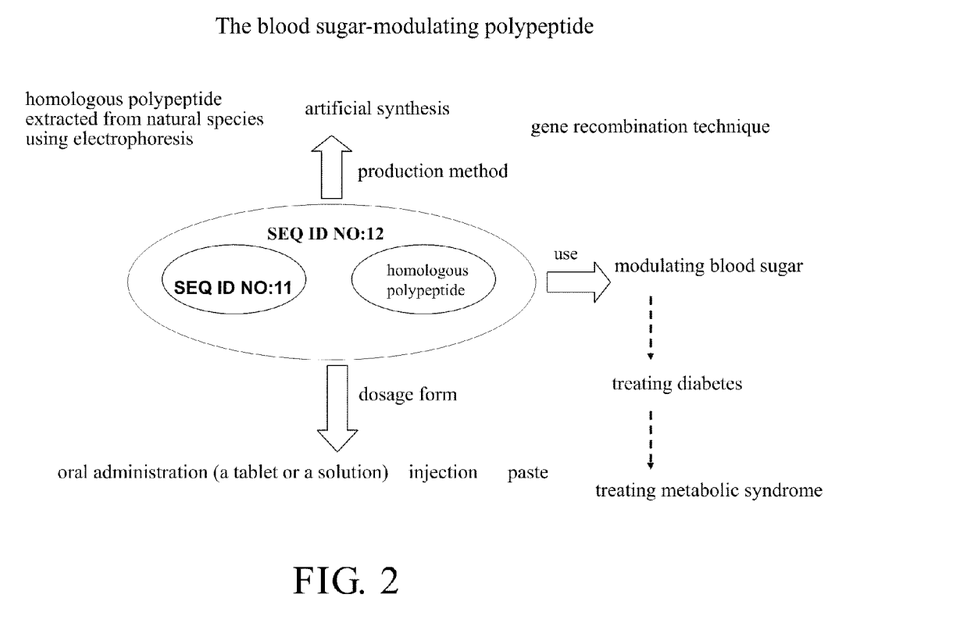
FIG. 2 is a figure illustrating the production method, the applicable dosage forms of the pharmaceutical composition, and the use of the polypeptide of the present invention.

FIG. 2 illustrates the production method, the applicable dosage forms of a pharmaceutical composition, and the use of the polypeptide of the present invention.

The present invention will be further illustrated in details with specific examples as follows. After referring to the examples described in the following paragraphs, people skilled in this field can easily appreciate the basic spirit and other invention purposes of the present invention, and technical methods adopted in the present invention and better embodiments. However, the following examples are provided only for illustrating the present invention, and the scope of the present invention is not limited thereby.

[Materials]

The following materials were adopted in the examples:
(A) Experimental subjects: two strains of mice, BALB/c (the metabolism of blood sugar is normal) and ob/ob (spontaneous diabetes type 2), were used to conduct experiments, and they were provided by the National Laboratory Animal Center, Taiwan.
(B) Polypeptides: polypeptides with amino acid sequences shown in Table 1 were produced by the solid phase synthesis method.

TABLE 1

| Sequence Number | Sequence |
| --- | --- |
| SEQ ID NO: 1 | RVRIWVNKRGLVVSPPRIG |
| SEQ ID NO: 2 | RVWVWVNSKGIVIRTPIIT |
| SEQ ID NO: 3 | RVWVWINKDEIVYQVPTIG |
| SEQ ID NO: 4 | RVRVWVDSYGIVSMVPKIG |
| SEQ ID NO: 5 | RVRVWVDENGIVISVPTIG |
| SEQ ID NO: 6 | RVRVWVNKKGKVIRVPRIG |
| SEQ ID NO: 7 | RVRVWVDENGIVTRVPVIG |
| SEQ ID NO: 8 | RVRVWVDEIRIVVRNPTAG |
| SEQ ID NO: 9 | DENRVRIWVDTVAKTPTIG |
| SEQ ID NO: 10 | RVRVWVTERGIVAR |
| SEQ ID NO: 11 | RVRVWVTERGIVARPPTIG |
| SEQ ID NO: 12 | SRCQGKSSWPQLVGSTGAAAKAVIERE NPRVRAVIIKVGSGATKDFRCDRVRVWV TERGIVARPPTIG |

Example 1

Five normal mice (BALB/c) fasted for 18 hrs and five diabetic mice (ob/ob) fasted for 4 hrs, respectively. Then, a solution (100 μL) of $2.5 \times 10^{-9}$ mole/kg-body weight of the polypeptide of SEQ ID NO: 12 was injected into the peritoneal cavity of each mouse of the experimental group, while in the control group (five mice), each mouse was injected with water (100 μL). After 15 minutes, a solution of 4 g/kg-body weight of glucose was injected into the peritoneal cavity of each normal mouse (BALB/c), while each diabetes mouse (ob/ob) was injected with a solution of 1 g/kg-body weight of glucose into the peritoneal cavity to rapidly raise the blood sugar value of each mouse. After 180 minutes, the blood of each mouse was extracted from its tails, and the blood sugar value was determined by a blood sugar meter (Accu-Check Advantage, Roche, Germany). The blood sugar values of the mice of the experimental group were compared with those of the control group and were analyzed to obtain a relative inhibition rate of the polypeptide of SEQ ID NO: 12 toward the blood sugar values, as shown in Table 2.

TABLE 2

| Sequence Number | Group | Inhibition Rate (%) |
| --- | --- | --- |
| SEQ ID NO: 12 | BALB/c | 68.6 ± 5.4* |
| SEQ ID NO: 12 | ob/ob | 51.0 ± 14.2* |

(the statistics was based on Student's t-test, $*p < 0.05$)

As shown in Table 2, in this experiment, both for the normal mice and the diabetic mice, the polypeptide of SEQ ID NO: 12 can decrease their blood sugar values efficiently. The polypeptide of SEQ ID NO: 12 can make the blood sugar values of the normal mice reach an inhibition rate of about 70%, and also can make the blood sugar values of the diabetic mice reach an inhibition rate of about 50%.

Example 2

Five normal mice (BALB/c) fasted for 18 hrs and five diabetic mice (ob/ob) fasted for 4 hrs, respectively. Then, a solution (100 μL) of $2.5 \times 10^{-9}$ mole/kg-body weight of the polypeptide of SEQ ID NO: 11 was injected into the peritoneal cavity of each mouse of the experimental group, while in the control group (five mice), each mouse was injected with water (100 μL). After 15 minutes, a solution of 4 g/kg-body weight of glucose was injected into the peritoneal cavity of each normal mouse (BALB/c), while each diabetic mouse (ob/ob) was injected with a solution of 1 g/kg-body weight of glucose into the peritoneal cavity, so as to raise the blood sugar value of each mouse rapidly. After 180 minutes, the blood of each mouse was extracted from its tails, and the blood sugar value was determined by a blood sugar meter (Accu-Check Advantage, Roche, Germany). The blood sugar values of the mice of the experimental group were compared with those of the control group and were analyzed to obtain a relative inhibition rate of the polypeptide of SEQ ID NO: 11 toward the blood sugar values, as shown in Table 3.

TABLE 3

| Sequence Number | Group | Inhibition Rate (%) |
| --- | --- | --- |
| SEQ ID NO: 11 | BALB/c | 54.1 ± 13.1*** |
| SEQ ID NO: 11 | ob/ob | 38.3 ± 13.5* |

(the statistics was based on Student's t-test, $*p < 0.05$, $***p < 0.001$)

As shown in Table 3, in this experiment, both for the normal mice and the diabetic mice, the polypeptide of SEQ ID NO: 11 can decrease their blood sugar values efficiently. The polypeptide of SEQ ID NO: 11 can make the blood sugar values of the normal mice reach an inhibition rate of about 50%, and also can make the blood sugar values of the diabetic mice reach an inhibition rate of about 40%.

Example 3

Five normal mice (BALB/c) in each of the nine groups fasted for 18 hrs, and then, respectively, a solution (20 μL) of 50 mg/kg-body weight of the polypeptide of SEQ ID NO: 1, a solution (20 μL) of 50 mg/kg-body weight of the polypeptide of SEQ ID NO: 2, a solution (20 μL) of 50 mg/kg-body weight of the polypeptide of SEQ ID NO: 3, a solution (20 μL) of 50 mg/kg-body weight of the polypeptide of SEQ ID NO: 4, a solution (20 μL) of 50 mg/kg-body weight of the polypeptide of SEQ ID NO: 5, a solution (20 μL) of 50 mg/kg-body weight of the polypeptide of SEQ ID NO: 6, a solution (20 μL) of 50 mg/kg-body weight of the polypeptide of SEQ ID NO: 7, a solution (20 μL) of 50 mg/kg-body weight of the polypeptide of SEQ ID NO: 8, or a solution (20 μL) of 50 mg/kg-body weight of the polypeptide of SEQ ID NO:9, was given to each mouse of each group of the experimental group by oral administration, while in the control group (five mice), each mouse was given water (20 μL). After 15 minutes, a solution of 4 g/kg-body weight of glucose was injected into the peritoneal cavity of each mouse to rapidly raise the blood sugar value of each mouse. After 180 minutes, the blood of each mouse was extracted from its tails, and the blood sugar value was determined by a blood sugar meter (Accu-Check Advantage, Roche, Germany). The blood sugar values of the mice of the experimental group were compared with those of the control group and were analyzed to obtain the relative inhibition rate of each of the polypeptides toward the blood sugar values, as shown in Table 4.

TABLE 4

| Sequence Number | Sequence | Inhibition Rate (%) |
| --- | --- | --- |
| SEQ ID NO: 1 | RVRIWVNKRGLVVSPPRIG | 15.7 ± 6.9 |
| SEQ ID NO: 2 | RVWVWVNSKGIVIRTPIIT | 24.5 ± 2.3 |
| SEQ ID NO: 3 | RVWVWINKDEIVYQVPTIG | 52.5 ± 14.9 |
| SEQ ID NO: 4 | RVRVWVDSYGIVSMVPKIG | 67.8 ± 9.1 |
| SEQ ID NO: 5 | RVRVWVDENGIVISVPTIG | 30.2 ± 31.3 |
| SEQ ID NO: 6 | RVRVWVNKKGKVIRVPRIG | 26.2 ± 3.1 |
| SEQ ID NO: 7 | RVRVWVDENGIVTRVPVIG | 56.3 ± 2.6 |
| SEQ ID NO: 8 | RVRVWVDEIRIVVRNPTAG | 25.5 ± 8.6 |
| SEQ ID NO: 9 | DENRVRIWVDTVAKTPTIG | 60.2 ± 14.1 |

As shown in Table 4, the polypeptides with an amino acid sequence of SEQ ID NO:4, SEQ ID NO:7, or SEQ ID NO:9 have a better effect of reducing the blood sugar values, and they are from different plant families. Thus, this experiment shows that polypeptides from plants can reduce the blood sugar value in the body.

Example 4

Five normal mice (BALB/c) in each of two groups fasted for 18 hrs, and then, respectively, a solution (20 µL) of 50 mg/kg-body weight of the polypeptide of SEQ ID NO: 10, or a solution (20 µL) of 50 mg/kg-body weight of the polypeptide of SEQ ID NO:11, was given to each mouse of each group of the experimental group by oral administration, while in the control group (five mice), each mouse was given water (20 µL). After 15 minutes, a solution of 4 g/kg-body weight of glucose was injected into the peritoneal cavity of each mouse to rapidly raise the blood sugar value of each mouse. After 180 minutes, the blood of each mouse was extracted from its tails, and the blood sugar value was determined by a blood sugar meter (Accu-Check Advantage, Roche, Germany). The blood sugar values of the mice of the experimental group were compared with those of the control group and were analyzed to obtain a relative inhibition rate of the polypeptides of SEQ ID NO:10 and SEQ ID NO:11 toward the blood sugar values, as shown in Table 5.

TABLE 5

| Sequence Number | Sequence | Inhibition Rate (%) |
| --- | --- | --- |
| SEQ ID NO: 10 | RVRVWVTERGIVAR | 34.5 ± 8.8** |
| SEQ ID NO: 11 | RVRVWVTERGIVARPPTIG | 51.9 ± 19.4** | the statistics was based on Student's t-test, **p < 0.01

As can be seen in Table 5, in this experiment, both the polypeptides of SEQ ID NO:10 and SEQ ID NO:11 can reduce the blood sugar values of the normal mice efficiently. The polypeptide of SEQ ID NO:11 can make the blood sugar values reach an inhibition rate of about 50%.

Example 5

Five normal mice (BALB/c) in each of fifteen groups fasted for 18 hrs, and then, respectively, an extract of bitter melon (cultivar: Yue-Hua) (20 µL) containing 1 g/kg-body weight of the polypeptide of the present invention (homologous polypeptides), an extract of bitter melon (cultivar: Tsuei-Fei) (20 µL) containing 1 g/kg-body weight of the polypeptide of the present invention (homologous polypeptides), an extract of bitter melon (cultivar: Siou-Hua) (20 µL) containing 1 g/kg-body weight of the polypeptide of the present invention (homologous polypeptides), an extract of kakorot (cultivar: OP) (20 µL) containing 1 g/kg-body weight of the polypeptide of the present invention (homologous polypeptides), an extract of kakorot (cultivar: WB15) (20 µL) containing 1 g/kg-body weight of the polypeptide of the present invention (homologous polypeptides), an extract of kakorot (cultivar: inbred line) (20 µL) containing 1 g/kg-body weight of the polypeptide of the present invention (homologous polypeptides), an extract of kakorot (cultivar: Hu2) (20 µL) containing 1 g/kg-body weight of the polypeptide of the present invention (homologous polypeptides), an extract of cucumber (cultivar: Wan-Lyu) (20 µL) containing 1 g/kg-body weight of the polypeptide of the present invention (homologous polypeptides), an extract of cucumber (cultivar: Si-Yan) (20 µL) containing 1 g/kg-body weight of the polypeptide of the present invention (homologous polypeptides), an extract of pumpkin (cultivar: Yi-Pin) (20 µL) containing 1 g/kg-body weight of the polypeptide of the present invention (homologous polypeptides), an extract of pumpkin (cultivar: Mu-Gua-Sing) (20 µL) containing 1 g/kg-body weight of the polypeptide of the present invention (homologous polypeptides), an extract of gourd (cultivar: Bian-Bo) (20 µL) containing 1 g/kg-body weight of the polypeptide of the present invention (homologous polypeptides), an extract of watermelon (cultivar: Fu-Bao) (20 µL) containing 1 g/kg-body weight of the polypeptide of the present invention (homologous polypeptides), an extract of watermelon (cultivar: Te-Siao-Fong) (20 µL) containing 1 g/kg-body weight of the polypeptide of the present invention (homologous polypeptides), or an extract of snake gourd seed (20 µL) containing 1 g/kg-body weight of the polypeptide of the present invention (homologous polypeptides) was given to each mouse of each group of the experimental group by oral administration, while in the control group (five mice), each mouse was given water (0.5 ml). After 15 minutes, a solution of 4 g/kg-body weight of glucose was injected into the peritoneal cavity of each mouse to rapidly raise the blood sugar value of each mouse. After 180 minutes, the blood of each mouse was extracted from its tails, and the blood sugar value was determined by a blood sugar meter (Accu-Check Advantage, Roche, Germany). The blood sugar values of the mice of the experimental group were compared with those of the control group and were analyzed to obtain the relative inhibition rate of each plant extract toward the blood sugar values, as shown in Table 6.

TABLE 6

| Plant (cultivar) | Inhibition Rate (%) |
| --- | --- |
| bitter melon (Yue-Hua) | 31.6 ± 16.6 |
| bitter melon (Tsuei-Fei) | 43.9 ± 12.9* |
| bitter melon (Siou-Hua) | 37.6 ± 24.3 |
| Kakorot (OP) | 30 ± 11.9* |
| Kakorot (WB15) | 21.7 ± 32.6 |
| Kakorot (inbred line) | 13.1 ± 21.8 |
| Kakorot (Hu2) | 12.9 ± 22.7 |
| cucumber (Wan-Lyu) | 24.3 ± 39.5 |
| cucumber (Si-Yan) | 10.1 ± 17.4 |
| pumpkin (Yi-Pin) | 50.5 ± 20.4* |
| pumpkin (Mu-Gua-Sing) | 33.8 ± 2.9** |
| gourd (Bian-Bo) | 51.5 ± 17.5* |
| watermelon (Fu-Bao) | 20 ± 4.9 |

TABLE 6-continued

| Plant (cultivar) | Inhibition Rate (%) |
| --- | --- |
| watermelon (Te-Siao-Fong) | 37.1 ± 20.7 |
| snake gourd seed | 6.5 ± 34.4 |

(the statistics was based on Student's t-test, *p < 0.05, **p < 0.01)

As can be seen in Table 6, all the plant extracts from the cucumber family, containing the polypeptide of the present invention, have the effect of reducing blood sugar. The extract of bitter melon (cultivar: Tsuei-Fei), the extract of pumpkin (cultivar: Yi-Pin), and the extract of gourd (cultivar: Bian-Bo) have better effects of reducing blood sugar.

From Examples 1 to 5, it is shown that administrating the polypeptide of the present invention through oral administration or peritoneal cavity injection in the normal mice (BALB/c) or the diabetic mice (ob/ob) may inhibit the high level of blood sugar caused by the attack of a high concentration of glucose.

The above examples are provided to illustrate the principle and efficacy of the subject invention, but not to limit the scope of protection thereof. People skilled in this field may proceed with a variety of modifications and replacements based on the above disclosures without departing from the principle and spirit of the subject invention. Therefore, the scope of protection of the subject invention is substantially covered in the following claims as appended.

What is claimed is:

1. A method for modulating blood sugar in a mammal, comprising selecting a mammal in need of regulation of blood sugar, and administering to the mammal an effective amount of a polypeptide comprising a following amino acid sequence:

RVRVWVTERGIVARPPTIG    (SEQ ID NO. 11).

2. The method as claimed in claim 1, which further comprises administering to the mammal a polypeptide comprising an amino acid sequence selected from a group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 12.

3. The method as claimed in claim 1, which further comprises administering to the mammal a polypeptide comprising an amino acid sequence selected from a group consisting of SEQ ID NO: 4, SEQ ID NO: 7, SEQ ID NO: 9, and SEQ ID NO: 12.

4. The method as claimed in claim 1, which further comprises administering to the mammal a polypeptide consisting of an amino acid sequence selected from a group consisting of SEQ ID NO: 4, SEQ ID NO: 7, SEQ ID NO: 9, and SEQ ID NO: 12.

5. The method as claimed in claim 1, wherein the polypeptide is obtained by a manner selected from a group consisting of plant extraction, artificial synthesis, gene recombination technique, and combinations thereof.

6. The method as claimed in claim 5, wherein the polypeptide is obtained by the extraction of a plant selected from a group consisting of bitter melon, kakorot, cucumber, pumpkin, gourd, watermelon, snake gourd seed, snake gourd root, and combinations thereof.

7. The method as claimed in claim 5, wherein the polypeptide is obtained by the extraction of a plant selected from a group consisting of *Zinnia elegans, Medicago truncatula*, grape, grapefruit, *Sambucus nigra, Arabidopsis thaliana*, rice, and combinations thereof.

8. The method as claimed in claim 5, wherein the gene recombination technique is carried out by the gene expression in a host cell, and the host cell is *Escherichia coli* or yeast.

9. The method as claimed in claim 1, wherein the polypeptide is administrated to the mammal in a form of a pharmaceutical composition.

10. The method as claimed in claim 9, wherein the pharmaceutical composition has a dosage form selected from a group consisting of a tablet, a capsule, a granule, a powder, a fluid extract, a solution, a syrup, a suspension, an emulsion, a tincture, an injection, an intravenous injection, a powder injection, a suspension injection, a powder-suspension injection, and combinations thereof.

11. The method as claimed in claim 1, which is for treating diabetes.

* * * * *

SEQUENCE LISTING

<160> NUMBER OF SEQ ID NOS: 13

<210> SEQ ID NO 1
<211> LENGTH: 19
<212> TYPE: PRT
<213> ORGANISM: CUCURBITA MAXIMA

<400> SEQUENCE: 1

Arg Val Arg Ile Trp Val Asn Lys Arg Gly Leu Val Val Ser Pro Pro
1               5                   10                  15

Arg Ile Gly

<210> SEQ ID NO 2
<211> LENGTH: 19
<212> TYPE: PRT
<213> ORGANISM: ZINNIA ELEGANS

<400> SEQUENCE: 2

Arg Val Trp Val Trp Val Asn Ser Lys Gly Ile Val Ile Arg Thr Pro
1               5                   10                  15

Ile Ile Thr

<210> SEQ ID NO 3
<211> LENGTH: 19
<212> TYPE: PRT
<213> ORGANISM: MEDICAGO TRUNCATULA

<400> SEQUENCE: 3

Arg Val Trp Val Trp Ile Asn Lys Asp Glu Ile Val Tyr Gln Val Pro
1               5                   10                  15

Thr Ile Gly

<210> SEQ ID NO 4
<211> LENGTH: 19
<212> TYPE: PRT
<213> ORGANISM: VITIS VINIFERA

<400> SEQUENCE: 4

Arg Val Arg Val Trp Val Asp Ser Tyr Gly Ile Val Ser Met Val Pro
1               5                   10                  15

Lys Ile Gly

<210> SEQ ID NO 5
<211> LENGTH: 19
<212> TYPE: PRT
<213> ORGANISM: VITIS VINIFERA

```
<400> SEQUENCE: 5

Arg Val Arg Val Trp Val Asp Glu Asn Gly Ile Val Ile Ser Val Pro
1               5                   10                  15

Thr Ile Gly

<210> SEQ ID NO 6
<211> LENGTH: 19
<212> TYPE: PRT
<213> ORGANISM: CITRUS PARADISI

<400> SEQUENCE: 6

Arg Val Arg Val Trp Val Asn Lys Lys Gly Lys Val Ile Arg Val Pro
1               5                   10                  15

Arg Ile Gly

<210> SEQ ID NO 7
<211> LENGTH: 19
<212> TYPE: PRT
<213> ORGANISM: SAMBUCUS NIGRA

<400> SEQUENCE: 7

Arg Val Arg Val Trp Val Asp Glu Asn Gly Ile Val Thr Arg Val Pro
1               5                   10                  15

Val Ile Gly

<210> SEQ ID NO 8
<211> LENGTH: 19
<212> TYPE: PRT
<213> ORGANISM: ARABIDOPSIS THALIANA

<400> SEQUENCE: 8

Arg Val Arg Val Trp Val Asp Glu Ile Arg Ile Val Val Arg Asn Pro
1               5                   10                  15

Thr Ala Gly

<210> SEQ ID NO 9
<211> LENGTH: 19
<212> TYPE: PRT
<213> ORGANISM: ORYZA SATIVA

<400> SEQUENCE: 9

Asp Glu Asn Arg Val Arg Ile Trp Val Asp Thr Val Ala Lys Thr Pro
1               5                   10                  15

Thr Ile Gly

<210> SEQ ID NO 10
<211> LENGTH: 14
<212> TYPE: PRT
<213> ORGANISM: MOMORDICA CHARANTIA

<400> SEQUENCE: 10

Arg Val Arg Val Trp Val Thr Glu Arg Gly Ile Val Ala Arg
1               5                   10

<210> SEQ ID NO 11
<211> LENGTH: 19
<212> TYPE: PRT
<213> ORGANISM: MOMORDICA CHARANTIA
```

```
-continued

<400> SEQUENCE: 11

Arg Val Arg Val Trp Val Thr Glu Arg Gly Ile Val Ala Arg Pro Pro
1               5                   10                  15

Thr Ile Gly

<210> SEQ ID NO 12
<211> LENGTH: 68
<212> TYPE: PRT
<213> ORGANISM: MOMORDICA CHARANTIA

<400> SEQUENCE: 12

Ser Arg Cys Gln Gly Lys Ser Ser Trp Pro Gln Leu Val Gly Ser Thr
1               5                   10                  15

Gly Ala Ala Ala Lys Ala Val Ile Glu Arg Glu Asn Pro Arg Val Arg
            20                  25                  30

Ala Val Ile Ile Lys Val Gly Ser Gly Ala Thr Lys Asp Phe Arg Cys
        35                  40                  45

Asp Arg Val Arg Val Trp Val Thr Glu Arg Gly Ile Val Ala Arg Pro
    50                  55                  60

Pro Thr Ile Gly
65

<210> SEQ ID NO 13
<211> LENGTH: 18
<212> TYPE: PRT
<213> ORGANISM: MOMORDICA CHARANTIA

<400> SEQUENCE: 13

Lys Thr Asn Met Lys His Met Ala Gly Ala Ala Ala Ala Gly Ala Val
1               5                   10                  15

Val Gly
```